United States Patent [19]

Tam

[11] Patent Number: 4,888,693
[45] Date of Patent: Dec. 19, 1989

[54] METHOD TO OBTAIN OBJECT BOUNDARY INFORMATION IN LIMITED-ANGLE COMPUTERIZED TOMOGRAPHY

[75] Inventor: Kwok C. Tam, Schenectady, N.Y.

[73] Assignee: General Electric Company, Schenectady, N.Y.

[21] Appl. No.: 32,804

[22] Filed: Apr. 1, 1987

[51] Int. Cl.[4] .......................... G06K 9/46; G06F 15/38
[52] U.S. Cl. ........................... 364/413.16; 364/413.13; 378/901
[58] Field of Search .................. 364/507, 414, 413.13, 364/413.16; 378/901; 367/507

[56] References Cited

U.S. PATENT DOCUMENTS 4,506,327  3/1985  Tam ................................... 364/414
4,672,651  6/1987  Horiba ................................ 364/414

OTHER PUBLICATIONS

Tam, K. C. and Perez-Mendez, V., "Tomographical Imaging with Limited-Angle Input", J. Opt. Soc. Am., 71 (May 1981) 582-592.

Primary Examiner—Jerry Smith
Assistant Examiner—Gail O. Hayes
Attorney, Agent, or Firm—Paul R. Webb, II; James C. Davis, Jr.

[57] ABSTRACT

A method is developed to construct the convex hull of an object in limited-angle x-ray computerized tomography. The convex hull is the smallest convex region containing the object, and therefore it can serve as a prior information on the object exterior boundary in reconstructing the object by an iterative limited-angle reconstruction procedure. The convex hull is the same as the exterior boundary of many convex objects and is a good approximation if the shape is not too concave. Greater accuracy is achieved by doing curve fitting near the edges of the x-ray projection data to determine the end points, and performing a low energy x-ray exposure at every scan angle in addition to the usual CT energy one. Over-attenuated x-ray data has utility in constructing the convex hull.

5 Claims, 5 Drawing Sheets

OVER-ATTENUATED $P_i$ $P_i$
FITTED CURVES
END POINTS

METHOD TO OBTAIN OBJECT BOUNDARY INFORMATION IN LIMITED-ANGLE COMPUTERIZED TOMOGRAPHY

BACKGROUND OF THE INVENTION

This invention relates to limited-angle image reconstruction and more particularly to a method to estimate the exterior boundary of an object and its use in limited-angle computerized tomography.

In some x-ray CT situations the x-ray data of the object is available only in a limited angular range. Limited-angle imaging occurs, for example, when scanning in some angular range is obstructed by other physical objects, or when the x-ray is attenuated too much in some angular range to serve any useful purpose. Under such circumstances limited-angle reconstruction techniques could be employed to reconstruct the object from x-ray data and other information about the object, such as: (1) exterior boundary of the object; (2) upper bound of the object density; and (3) lower bound of the object density. It has been shown that by using this information in addition to the limited-angle x-ray data, the object may be reconstructed uniquely; refer to Tam, K.C. and Perez-Mendez, V., J. Opt. Soc. Am., 71 (1981) 582-592. One limited-angle reconstruction algorithm developed in this reference is shown in FIG. 1; the image is transformed back and forth between the object space by filtered back-projection, and the projection space by projection, being corrected by the a priori information in the object space, and the limited-angle known projections in the projection space.

The upper and lower bounds of the object density are usually available. For example, they can be estimated from the a priori knowledge about the composition of the object; in fact the lower bound is usually taken to be zero. Currently there is no systematic method to obtain the object boundary. In the literature it is simply assumed the object boundary can be estimated one way or another. Some of the methods mentioned include probing, modeling, etc., which all involve additional equipment and which may not yield the boundary of the object actually imaged.

The inventor's copending application Ser. No. 877,083, filed June 23, 1986, "Method for Reconstructing Objects from Limited-Angle Scannings in Computerized Tomography", now abandoned, and continuation application Ser. No. 205,398, filed June 10, 1988, relates to an object to be imaged which contains a medium that occupies most of the cross-sectional area and the density of the medium is usually known, for instance a metal medium with embedded flaws. Under these circumstances image reconstruction of the flaw is improved by constructing a flaw-enclosing region; since knowledge of the region of occurrence of the flaw is more precise, using the flaw-enclosing region as a priori information yields better results than if the much larger object boundary were used. This method assumes the boundary of the object is known exactly.

SUMMARY OF THE INVENTION

An object of this invention is to prescribe, in limited-angle CT, a procedure to estimate the exterior boundary of the object using x-ray data without any additional equipment.

Another object is to develop a method to construct the convex hull of an object and use it in limited-angle reconstruction algorithms as an approximation to the actual object boundary. The convex hull of an object is the smallest convex region containing the object and therefore can serve as boundary information in reconstructing the object.

Yet another object is to define techniques to reduce the effect of noise and improve the definition of non-zero regions in the x-ray data from which the convex hull is produced.

One aspect of the present invention is a method to reconstruct an object in limited-angle CT comprising: exposing the object to x-rays at scanning angles within an allowed angular range and generating detected x-ray data and a measured projection at every angle; backprojecting the last-mentioned to yield a backprojection strip which contains the support of the object, i.e the region where object density is non-zero; intersecting or superimposing all the backprojection strips to construct a polygon-shaped region which completely contains the object and is an approximation of the convex hull of the object; and reconstructing the object by means of a limited-angle reconstruction procedure involving repeated transformations between object space and projection space, correcting the reconstructed image in object space by a priori information comprised of the constructed polygon-shaped region and the upper and lower bounds of object density, and in projection space by the measured projections.

Many industrial (and medical) objects are convex in shape, and in this case the constructed polygonal-region approximates the object exterior boundary. Even if the object is not convex, the constructed region is still a good approximation to the exterior boundary if the boundary is not too concave.

Another feature of the invention is that where the limited-angle restriction is caused by serious attenuation of x-rays in some angular range, even the over-attenuated x-ray data can be used to construct the convex hull of the object. The transition region between where the measured projection is zero and 10 where it is non-zero is more distinct in over-attenuated x-ray data and thus is well suited for the purpose of constructing the object convex hull. However, the limited-angle reconstruction procedure utilizes the measured projections at only those scan angles where there is no serious attenuation of x-rays.

Another feature is that the convex hull and object exterior boundary are estimated with greater accuracy by fitting curves to the edges of the projection data to determine the two end points between attenuated and unattenuated x-rays. This reduces instabilities caused by noise. The data between the two end points is backprojected.

Yet another aspect of the invention is to use low energy x-ray data to estimate the object boundary, because the object is more opaque to such rays and the edges are sharper in the low energy exposure. At each scanning angle a low energy x-ray exposure is performed in addition to the one at the usual CT energy. The low energy projection data is processed by curve fitting at the edges, and the data between the more precisely determined end points is backprojected to yield a backprojection strip which contains the support of the object. All of the backprojection strips at angles within the allowed angular range are overlapped to construct the polygon-shaped region which approximates the convex hull. The object is reconstructed and displayed by means of a limited-angle image reconstruction technique using (1) the constructed region as object exterior boundry information; (2) the usual CT energy x-ray data and scanning angles, and (3) other a priori information on object density.

DETAILED DESCRIPTION OF THE INVENTION

Figure 2:
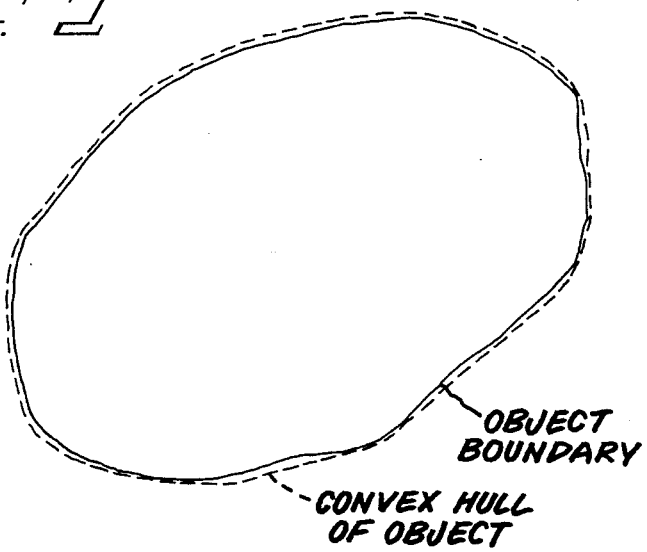
FIG. 2 illustrates the convex hull of a 2-dimensional object.

As illustrated in FIG. 2, the convex hull of a two-dimensional object is the smallest convex region containing the object. The approach taken in this invention is to construct the convex hull of the object using the x-ray data, and use the convex hull as an approximation to the actual object boundary. In medical applications, the cross-section of the human body or the cross-section of the skull is mostly convex. Most of the industrial objects are convex in shape, such as cylinders, spheroids, parallelepipeds, etc. In this case the convex hull is the same as the object boundary. Even if the object is not completely convex, the convex hull is still a good approximation of the object exterior boundary if the shape is not too concave. Hence the use of the object convex hull as an approximation to the object boundary is justified. Convex hull is defined in the McGraw-Hill Dictionary of Scientific and Technical Terms, 1978, as "the smallest convex set containing a given collection of points in a real linear space". The mathematical definition of support is: "The support of a real-valued function f on a topological space is the closure of the set of points where f is not zero".

Figure 3:
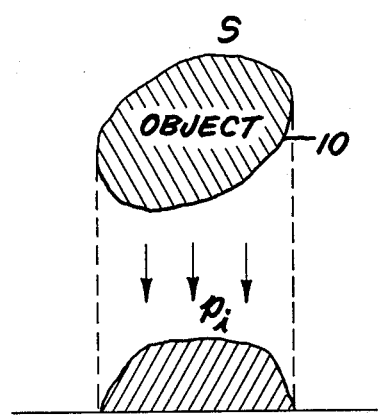
FIG. 3 shows the support of an object, i.e. the region where the object density is non-zero, and the x-ray projection data of the object at a given angle.
Figure 4:
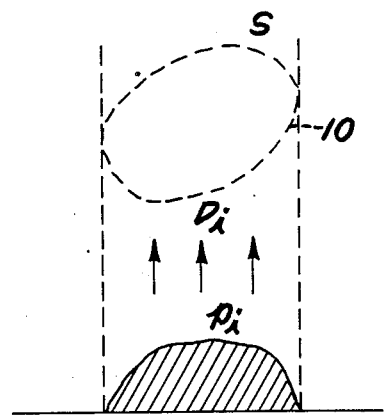
FIG. 4 shows the backprojection of the projection data.
Figure 5:
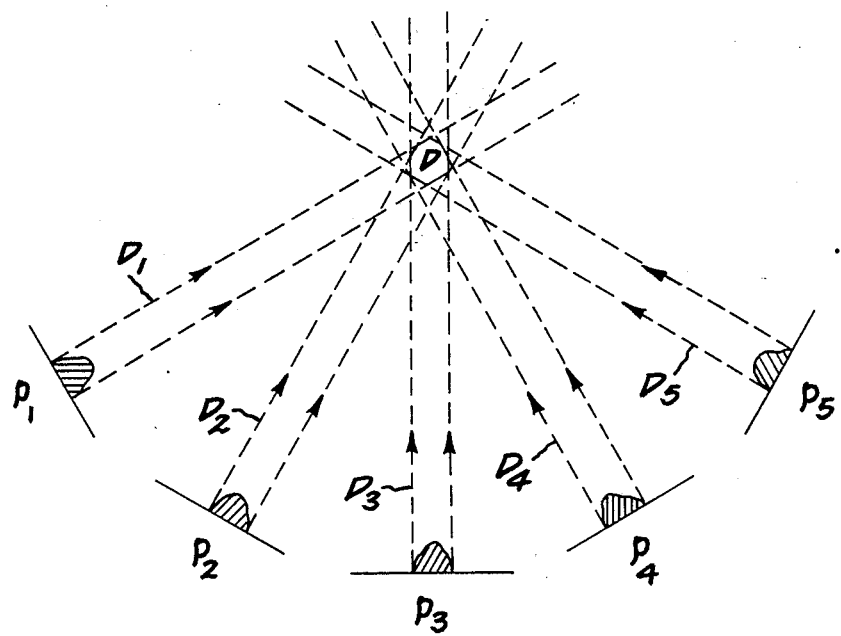
FIG. 5 illustrates constructing a region which contains the object and approaches the convex hull of the object.

The technique of estimating the exterior boundary of the object from the x-ray data without using any additional equipment is illustrated in FIGS. 3–5. S represents the support of the object 10, i.e. the region where the object density is non-zero, and $p_i$ represents x-ray projection data of the object at angle $\theta_i$. The non-zero portion $D_i$ of the backprojection of the projection data $p_i$ is shown in FIG. 4. It follows that the support S of the object is completely contained within the backprojection strip $D_i$.

FIG. 5 shows five projections $p_1$ to $p_5$ taken at five different viewing angles and the backprojection strips $D_1$ to $D_5$ obtained by backprojecting the non-zero portion of the projection data. If one constructs a region D by intersecting all of the backprojection strips, it follows that the support of the object is contained entirely within region D. Thus we have succeeded in constructing a region D which completely contains the object. It is obvious from the above construction procedure that: (1) region D is a polygon containing the object; and (2) as the number of projection angles increases, region D approaches the boundary of the object if the boundary is convex. If the boundary is not convex, region D approaches the convex hull of the boundary.

Figure 1:
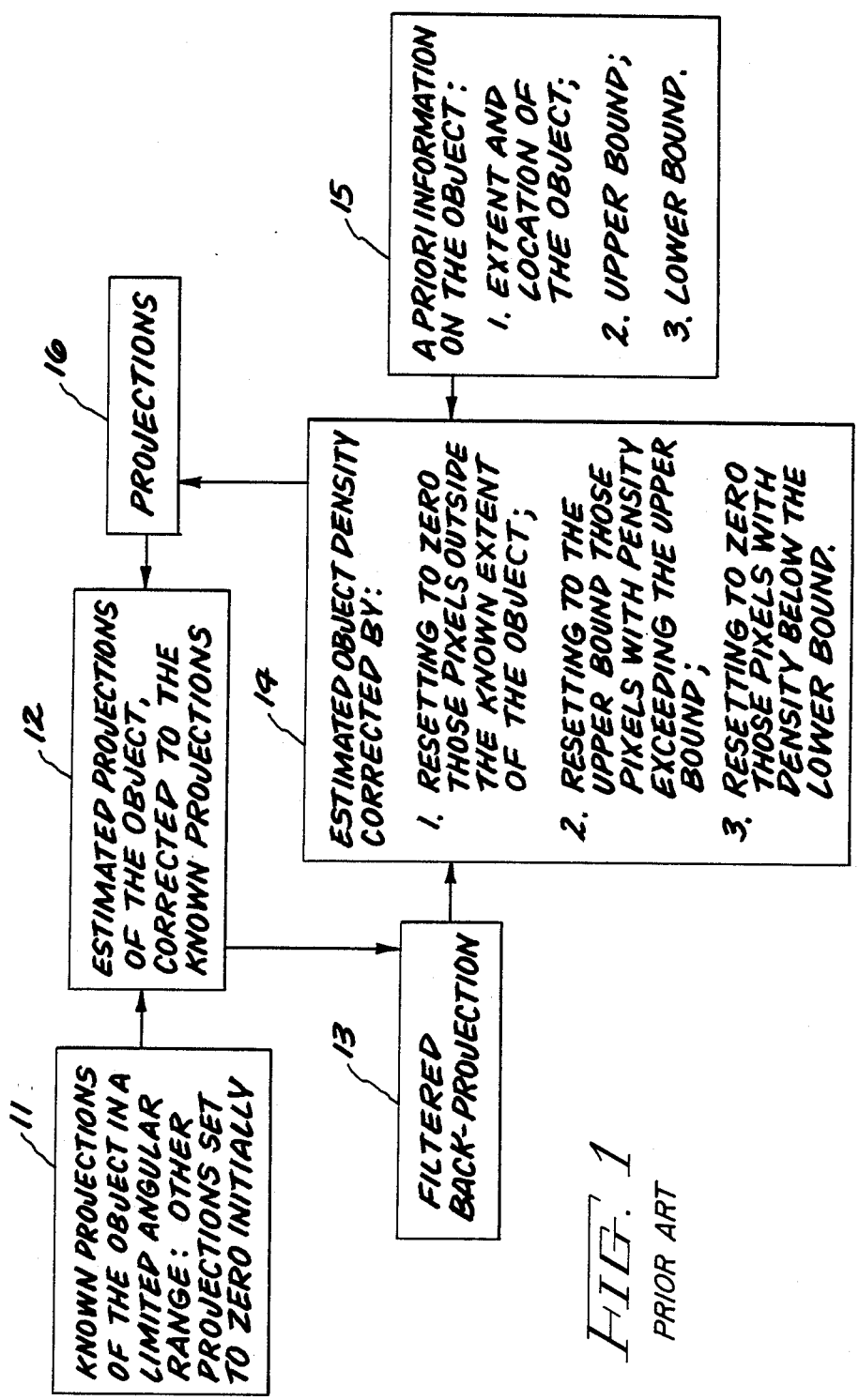
FIG. 1 is a flowchart of a limited-angle reconstruction procedure using an iterative transform algorithm.

The object is reconstructed and displayed by means of the limited-angle reconstruction procedure diagrammed in FIG. 1; the cited Tam and Perez-Mendez published paper is incorporated by reference herein. The constructed polygon-shaped region D is utilized as a priori information on the extent and location of the object, and in particular as information on the external boundary of the object. Other known a priori information on the object are the upper and lower bounds of the object density. This is an iterative algorithm: the reconstructed image is transformed back and forth between the object space by filtered backprojection, and the projection space by projection, being repeatedly corrected by the a priori information about the object in the object space and by the known or measured projections in the projection space. The measured projections $p_1$ to $p_5$ of the object in the limited angular range are provided, and the other missing projections to make up a complete 180° angular range are set to zero initially as shown in block 11. A first iteration simply uses the known projection data which is derived from the detected x-ray data by taking the negative of the logarithm. These are provided from block 12 to block 13 wherein a filtered backprojection operation is performed to determine a first estimate of object density. This first iterate is corrected to take into account the a priori information on the object shown in block 15.

Figure 6:
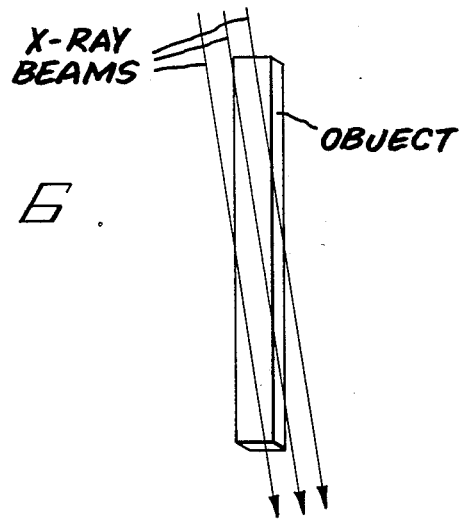
FIG. 6 shows a long narrow object which causes serious attenuation of the x-ray beam in an angular range.
Figure 7:
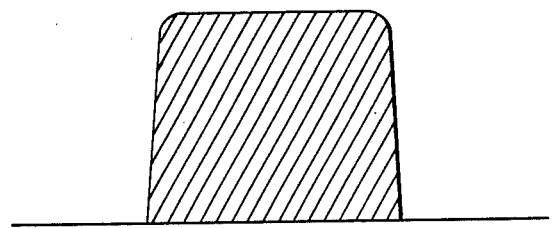
FIG. 7 illustrates the over-attenuated projection data of such an object.

The first iterate of object density is corrected by resetting to zero those pixels outside the known extent of the object, the constructed polygon-shaped region which approximates the exterior boundary of the object; resetting to the upper bound those pixels with density exceeding the upper bound; and resetting to zero those pixels with density below the lower bound. From this second estimate of object density the projections in the supplementary, missing angles are calculated and the reconstructed image is transformed back to projection space by a projection operation at block 16. The calculated projections of the supplementary angles are combined with the known, measured projection data at other angles to yield a new estimate of object density, and the process is repeated. The cycling between the projection space and object space continues in the loop illustrated by blocks 12, 13, 14 and 16 until the object reconstruction is sufficiently precise; usually ten to twenty iterations are performed but a check for convergence may be made and used to stop the cycling if, for example, the object density changes less than a given percentage from one iteration to the next iteration.

Where the limited-angle restriction is caused by the serious attenuation of the x-ray beam in some angular range, then even the over-attenuated detected x-ray data can be used in the above procedure to construct the polygonal region D and convex hull of the object. For instance, referring to FIG. 6, in industrial x-ray CT the object may be elongated such that there is too much attenuation for x-ray beams at large oblique incidence angles. The reason is that in constructing the backprojection strips $D_i$ in FIG. 4, all that is needed is the knowledge of the non-zero region in the measured projection data $p_i$, their numerical value being irrelevant. Such information is present even in the over-attenuated x-ray data $p_i$, as illustrated in FIG. 7. In fact, the transition region between the region where the projection is zero and the region where the projection is non-zero is more distinct in the over-attenuated x-ray data, and thus such data are better suited for the purpose of constructing the object convex hull.

A limited-angle imaging method to more accurately reconstruct an object that seriously attenuates x-rays in some angular range is as follows. The object is scanned with x-rays at angles over a full 180° range, or at angles within the allowed range, and detected x-ray data and projection data are generated at every scan angle. All of the measured projections are backprojected to yield backprojection strips each of which contains the support of the object. All of the backprojection strips are overlapped, either intersected or superimposed, to construct the polygon-shaped region D which is the convex hull of the object. To reconstruct the object by means of the limited-angle image reconstruction procedure already described, only those measured projections at scan angles where there is no serious attenuation of x-rays are used, since the others contain no information on object density. A higher quality image results because the object exterior boundary is determined more precisely.

In the absence of noise, constructing the convex hull of an object by intersecting the backprojections of the non-zero projection data is a simple and fast procedure; at the end of the intersection process the convex hull is already formed. However, it may be unstable with respect to noise. The reason is that since the constructed region D is formed by intersection, the errors in the projection data combine multiplicitively. In other words, the pixel has to be contained within the backprojection strip $D_i$ of every projection $p_i$ in order to be included in the convex hull; it would be lost from the convex hull if it is not included in just one backprojection strip due to error in the corresponding projection $p_i$. This procedure can only underestimate the actual convex hull and therefore possibly the actual support and object boundary. For a priori information input to limited-angle image reconstruction, underestimating the object boundary is more serious than overestimating it.

An alternate method to construct the polygon-shaped region D is by superimposing the backprojection strips $D_i$ instead of intersecting them. Any pixel in the region D belongs to every backprojection strip $D_i$, and every pixel outside D is excluded from at least one strip $D_i$. Therefore one way to characterize the region D is to count the number of backprojection strips the pixel belongs to, and the pixel is assigned to D if the total number equals the number of backprojection strips. The advantage of this alternate procedure for constructing the region D is that the errors in the projections $p_i$ will combine additively instead of multiplicatively as in the intersection procedure. In the presence of noise, a pixel in D might be missed by some of the projections, and the criterion just discussed is relaxed so that the number of backprojection strips $D_i$ the pixel is found to belong to is less than the number of backprojection strips.

To further reduce the effect of noise and to improve the definition of the non-zero region in each measured projection $p_i$ and the accuracy of the estimated object exterior boundary, the following procedures can be adopted.

(1) Use low energy x-rays. At each scanning angle a low energy x-ray exposure is performed in addition to the one at usual CT energy. Since the object is much more opaque to low energy x-rays, the edges are therefore sharper in the low energy exposure.

Figure 8:
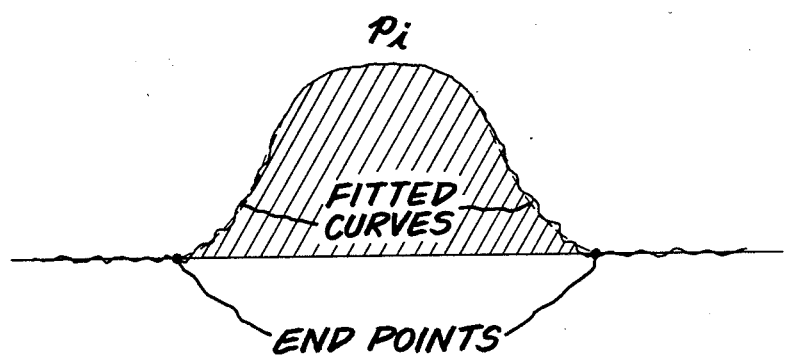
FIG. 8 illustrates curve fitting to more accurately determine end points of the x-ray projection data.

(2) To reduce instability caused by noise, curve fittings are made near the edges of the x-ray projection data $p_i$ to determine the end points between attenuated and unattenuated x-rays, as shown in FIG. 8.

Even though parallel beam scanning is illustrated, the invention is equally applicable to fan beam scanning without any modification. Complete data in a fan beam scan is obtained by scanning over a 360° angular range. The reason that a 360° rather than a 180° angular range is needed in a fan beam scan is that there is no mirror symmetry in the fan beam data (such symmetry exists in the parallel beam data).

Figure 9:
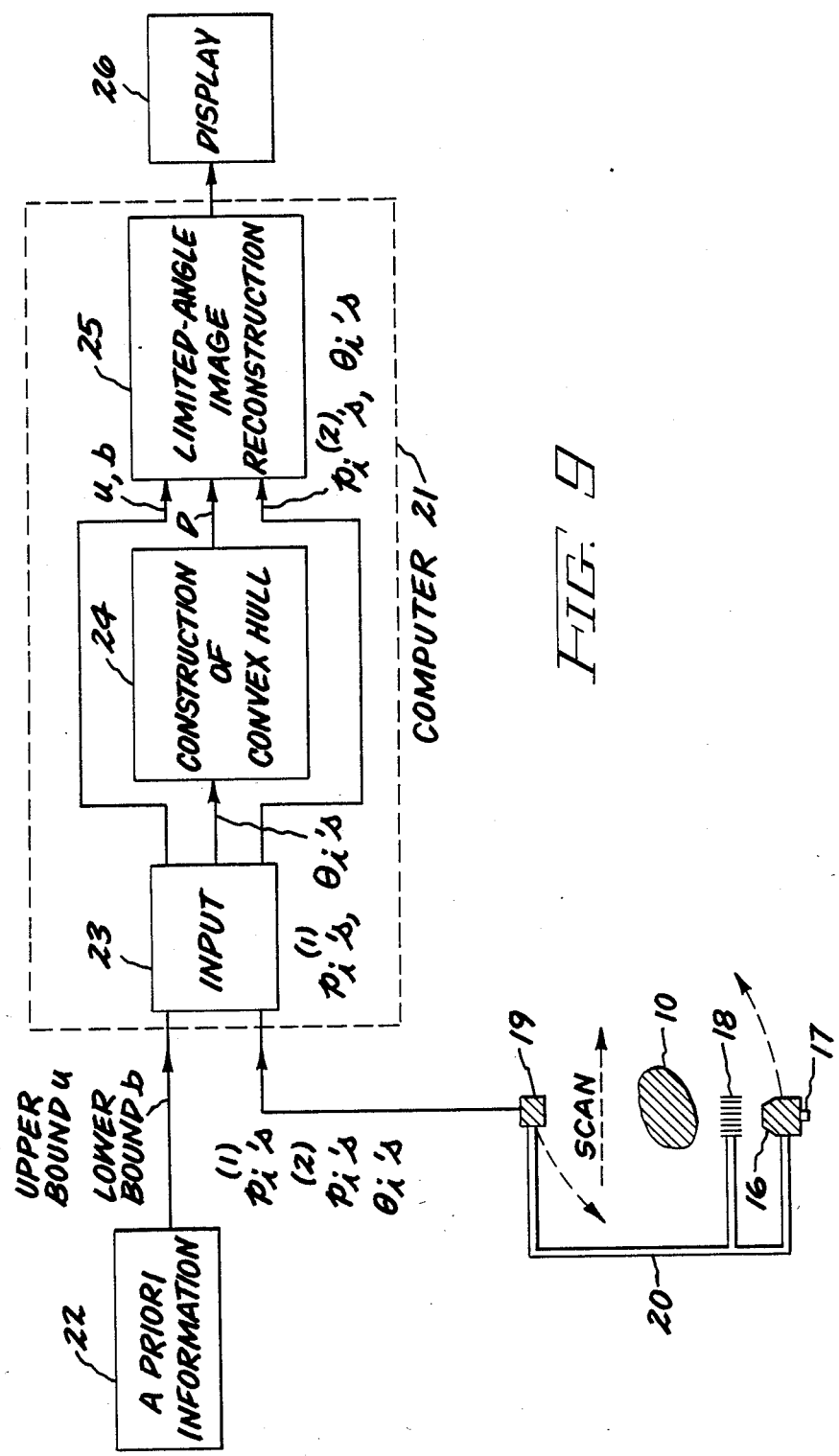
FIG. 9 is a diagram of an x-ray computerized tomography system for industrial nondestructive evaluation embodying this invention.

In FIG. 9 is shown one practical realization and embodiment of the invention, an industrial x-ray CT system. An x-ray source 16 has an energy switch 17 for selecting the beam energy and at each scanning angle the object is exposed to low energy x-rays and also to the usual CT energy x-rays. The x-ray beam is collimated at 18 into parallel rays and passes through the object 10 and is detected by an x-ray detector 19. The source, collimator and detector are mounted on a yoke 20 and moved linearly to scan the object, then rotated to change the scan angle to make a second linear scan, and so on. The object is scanned at many angles within the restricted angular range. The detected signals consist of the x-ray projection data $p_i^{(1)}$ and $p_i^{(2)}$ of the object at all the physically accessible angles $\theta_i$, i=1, 2, 3 etc., at the low energy and CT energy respectively. These are fed into processing computer 21 together with the values of the scanning angles $\theta_i$, and a priori information (block 22) on the upper and lower bounds u and b of the object density. The low energy projection data $p_i^{(1)}$ and the scanning angles $\theta_i$ are passed from the computer input (block 23) to convex hull construction logic (block 24) where the polygon-shaped region D, which is a convex hull approximation, is constructed using the following procedure:

(1) polynomial fit the edges of the low energy x-ray data $p_i^{(1)}$ at angle $\theta_i$ to determine the two end points between attenuated and unattenuated x-rays as shown in FIG. 8. This is done at all the available scan angles.

(2) Backproject the region within the edges and between the end points to form the backprojection strip $D_i$.

(3) Repeat steps (1) and (2) and form the polygon-shaped region D by intersecting all the backprojection strips $D_i$. Alternatively D is constructed by superimposing strips $D_i$. It is emphasized that the constructed region which serves as information on the exterior boundary of the object is computed from the low energy projection data only.

The object is reconstructed by the limited-angle image reconstruction logic (block 25) using the constructed region D, the usual CT energy x-ray data $p_i^{(2)}$ and scan angles $\theta_i$, and the a priori information on the upper and lower bounds of the object density. That the projection data obtained from the CT energy x-ray data is actually used in the algorithm is already explained with regard to FIG. 1. The image of the reconstructed object is displayed on a TV monitor or other suitable display device (block 26).

The application of x-ray CT to industrial nondestructive evaluation is growing in recent years. Limited-angle x-ray imaging occurs frequently in industrial inspection. The invention can be employed to obtain the boundary information of an object from the x-ray data without requiring additional equipment; this information is needed in reconstructing the object.

While the invention has been particularly shown and described with reference to preferred embodiments thereof, it will be understood by those skilled in the art that the foregoing and other changes in form and details may be made without departing from the spirit and scope of the invention.

The invention claimed is:

1. A method of obtaining object boundary information in limited-angle x-ray computerized tomography comprising:

exposing said object to x-rays at multiple scanning angles within a limited angular range and generating x-ray projection data;

processing, said projection data by doing curve fitting near the edges to more precisely determine end points between attenuated and unattenuated x-rays;

backprojecting the projection data between said end points at every scanning angle to yield a backprojection strip which contains the support of said object, defined as the region where object density is non-zero;

overlapping all of said backprojection strips to construct a region which is a polygon and the convex hull of said object, the smallest convex region containing said object; and using said constructed region as a priori information on the extent and location of said object and other a priori information, reconstruct and display said object by means of a limited-angle reconstruction technique.

2. The method of claim 1 wherein said object has a convex exterior boundary which is given by said constructed region.

3. The method of claim 1 wherein said object has an exterior boundary that is not convex and said constructed region approximates the exterior boundary of said object.

4. A method of reconstructing high quality images in a limited-angle x-ray computerized tomography (CT) system comprising:

exposing an object to low energy x-rays and to usual CT energy x-rays at many scanning angles over a limited angular range and generating x-ray projection data at both exposures;

processing said low energy projection data by fitting curves to the edges to more accurately determine the end points between attenuated and unattenuated x-rays;

backprojecting the low energy projection data between said end points to form, at every scanning angle, a backprojection strip which contains the support of said object, the region where object density is non-zero;

intersecting or superimposing all of said backprojection strips to construct a polygon-shaped region which is the convex hull of said object and the smallest convex region containing said object; and reconstructing and displaying said object by means of a limited-angle reconstruction procedure using (1) said constructed region as a priori information on the exterior boundary of said object, (2) the usual CT energy x-ray data and scanning angles, and (3) other a priori information.

5. The method of claim 4 wherein said other a priori information is the upper and lower bounds of object density.

* * * * *